United States Patent
Geller

(10) Patent No.: US 9,192,385 B2
(45) Date of Patent: *Nov. 24, 2015

(54) DEVICE AND METHOD TO FACILITATE SAFE, ADHESION-FREE SURGICAL CLOSURES

(76) Inventor: Evan Richard Geller, Stony Brook, NY (US)

(*) Notice: Subject to any disclaimer, the term of this patent is extended or adjusted under 35 U.S.C. 154(b) by 32 days.

This patent is subject to a terminal disclaimer.

(21) Appl. No.: 13/229,381

(22) Filed: Sep. 9, 2011

(65) Prior Publication Data

US 2012/0089178 A1    Apr. 12, 2012

Related U.S. Application Data

(60) Provisional application No. 61/392,168, filed on Oct. 12, 2010.

(51) Int. Cl.
| A61B 17/08 | (2006.01) |
| A61L 31/04 | (2006.01) |
| A61L 31/10 | (2006.01) |
| A61B 17/04 | (2006.01) |
| A61K 31/10 | (2006.01) |
| A61B 17/00 | (2006.01) |

(52) U.S. Cl.
CPC ............ *A61B 17/08* (2013.01); *A61B 17/0493* (2013.01); *A61K 31/10* (2013.01); *A61L 31/042* (2013.01); *A61L 31/10* (2013.01); *A61B 2017/00004* (2013.01)

(58) Field of Classification Search
None
See application file for complete search history.

(56) References Cited

U.S. PATENT DOCUMENTS

| 3,288,131 A | 11/1966 | Garland |
| 3,863,639 A * | 2/1975 | Kleaveland ............... 128/850 |
| 3,882,855 A | 5/1975 | Schulte et al. |
| 4,533,356 A | 8/1985 | Bengmark et al. |
| 4,747,393 A | 5/1988 | Medwid |
| 4,840,626 A | 6/1989 | Linsky et al. |
| 4,964,417 A | 10/1990 | Peters |

(Continued)

FOREIGN PATENT DOCUMENTS

CA    2733573 A1 *  3/2010

OTHER PUBLICATIONS

International Search Report and Written Opinion of PCT/US2011/055755 dated Jan. 19, 2012, 7 pages.

*Primary Examiner* — Bethany Barham
*Assistant Examiner* — Dominic Lazaro
(74) *Attorney, Agent, or Firm* — Baker & Hostetler LLP

(57) ABSTRACT

Surgical devices and methods are provided for preventing the formation of post-operative adhesions. In one device, an envelope of bioabsorbable material defines at least one opening, and a layer of bioabsorbable adhesion-preventing material is disposed on an exterior surface of the envelope. A rigid or semi-rigid barrier member is at least partially disposed in a space inside the envelope, without adhering to the envelope such that the barrier member can be pulled out of the envelope through the opening. In another device, a rigid or semi-rigid barrier member is removably attached to a layer of bioabsorbable adhesion-preventing material by a controlled adhesive. In another device, a rigid or semi-rigid bioabsorbable barrier member, such as compressed cellulose, is attached to a layer of bioabsorbable adhesion-preventing material. The envelope of bioabsorbable material may include cellulose or oxidized regenerated cellulose. The adhesion-preventing material may include chemically modified sodium hyaluronate and carboxymethylcellulose.

2 Claims, 3 Drawing Sheets

(56) References Cited

U.S. PATENT DOCUMENTS

| | | | |
|---|---|---|---|
| 5,002,551 A | 3/1991 | Linsky et al. | |
| 5,593,441 A | 1/1997 | Lichtenstein et al. | |
| 5,984,942 A * | 11/1999 | Alden et al. | 606/190 |
| 6,383,201 B1 | 5/2002 | Dong | |
| 6,736,141 B2 * | 5/2004 | Freedman | 128/850 |
| 2002/0077635 A1 | 6/2002 | Freedman | |
| 2003/0078602 A1 | 4/2003 | Rousseau | |
| 2004/0019360 A1 * | 1/2004 | Farnsworth et al. | 606/151 |
| 2006/0241689 A1 | 10/2006 | Leiboff et al. | |
| 2007/0061002 A1 | 3/2007 | Paul et al. | |
| 2007/0141156 A1 * | 6/2007 | Herzberg et al. | 424/486 |
| 2008/0069857 A1 * | 3/2008 | Yeo et al. | 424/426 |
| 2008/0254091 A1 | 10/2008 | Lee et al. | |
| 2009/0318843 A1 | 12/2009 | Van Holten et al. | |
| 2011/0152897 A1 * | 6/2011 | Bates | 606/151 |

* cited by examiner

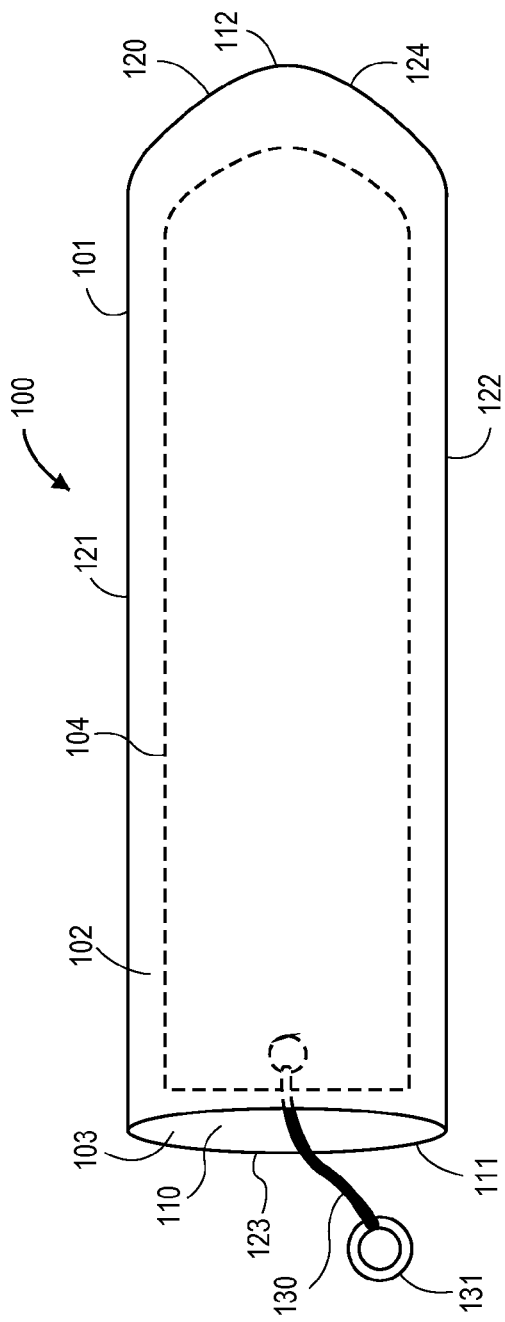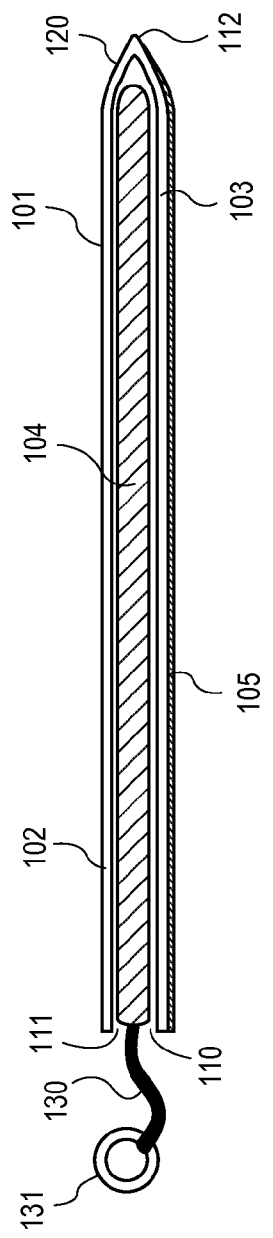

DEVICE AND METHOD TO FACILITATE SAFE, ADHESION-FREE SURGICAL CLOSURES

CROSS REFERENCE TO RELATED APPLICATION

This application claims priority to earlier filed U.S. Provisional Patent Application No. 61/392,168, filed on Oct. 12, 2010, the disclosure of which is hereby incorporated by reference, in its entirety.

FIELD OF THE INVENTION

The present invention generally relates to surgical medical devices for retracting tissue, preventing post-operative adhesions of tissue, and methods for same in closures of surgical incisions.

BACKGROUND

Two problems frequently encountered during the closure of surgical incisions of the abdomen are risk of injury to the bowel and the postoperative formation of adhesions to the abdominal wall.

Bowel injury leads to significant risk of infection, poor wound healing, hernia formation, and death. Bowel injury may be undetected at the time of surgery, leading to leakage of intestinal content into the abdominal cavity with resulting infection. If not diagnosed and treated promptly, this type of bowel injury carries a high risk of peritonitis, poor wound healing, hernia formation, and possible death. A mechanical barrier placed within the abdominal cavity prior to surgical closure of the abdominal wound reduces the risk of bowel injury during closure. Currently, surgeons occasionally utilize various barrier type devices during the closure of the abdomen to reduce the risk of bowel injury. These devices may be rigid such as a flat steel surgical retractor. Semi-rigid devices made of rubber or plastic are also utilized for this purpose, examples of which are shown in U.S. Pat. Nos. 4,964,417 and 4,747,393. These devices are not bioabsorbable and must be removed prior to completion of the surgical closure of the abdomen and therefore ultimately do not reduce the risk of postoperative adhesions. Surgical closure of the abdomen performed with the assistance of these currently available devices carries a significant risk of postoperative adhesion formation which may result in bowel obstruction.

Postoperative adhesions are the most frequent cause of small bowel obstruction, a common condition with significant morbidity and mortality, often requiring surgical intervention. The majority of these patients suffer obstruction due to intra-abdominal adhesions. These adhesions are the result of scar formation frequently associated with prior abdominal surgery. Bowel obstruction due to abdominal adhesions causes pain, vomiting, and may lead to gangrene of the bowel. Bowel obstruction due to adhesions frequently requires surgical treatment which may lead to a recurrent cycle of scar formation, obstruction, and surgery. A product which prevents the development of adhesions between the bowel and abdominal wall may be placed within the abdominal cavity prior to surgical closure of abdomen. Such a product may be a prosthesis made of silicone elastomer and/or polypropylene mesh fabric, such as disclosed in U.S. Pat. No. 5,593,441. Such a device however is not bioabsorbable. Currently, surgeons occasionally utilize various adhesion preventing materials during the closure of the abdomen to reduce the risk of postoperative adhesions. Products known to be effective in the prevention of adhesions include chemically modified sodium hyaluronate and carboxymethylcellulose, such as provided in SEPRAFILM® brand adhesion barrier manufactured by Genzyme Corporation, Cambridge, Mass. However, these materials are difficult to apply, being extremely friable, and having a tendency to stick to any surgical instrument once wetted after contacting tissue. Such a material also generally is provided as a thin layer or coating of material which is easily penetrated and therefore does not reduce the risk of injury to the bowel or other underlying tissue during closure of a surgical incision.

There currently exists no device which addresses all of the aforementioned problems during the closure of a surgical incision, such as in abdominal surgery. Efforts to employ current adhesion-preventing materials with current barrier devices leads to displacement of the adhesion-preventing material, rendering it ineffective. There remains a need therefore for a surgical device and method which reliably prevents injury to the bowel or viscera during closure of a surgical incision, while also aiding in reducing or preventing postoperative surgical adhesions.

SUMMARY OF THE INVENTION

The foregoing needs are met, to a great extent, by the present invention, wherein in some embodiments a surgical medical device and method that is capable of overcoming the disadvantages described herein at least to some extent is provided. The device facilitates the safe closure of surgical incisions in the abdominal cavity with the capacity to prevent the formation of postoperative adhesions. For example, the device combines a barrier function which serves to protect the bowel or viscera from injury during surgical closure of the abdomen with delivery of a product which prevents formation of adhesions postoperatively. The device may also be employed on other parts of the body, such as in the closure of thoracic incisions to prevent lung injury and adhesion formation to the lung. The device is easily utilized, safe, and cost effective.

In accordance with a first embodiment of the invention, a surgical device includes an envelope of bioabsorbable material having a first sheet connected to a second sheet and defining at least one opening between said sheets at a first end of the envelope. A layer of bioabsorbable adhesion-preventing material is disposed on at least the first sheet on an exterior surface of the envelope. A rigid or semi-rigid barrier member is at least partially disposed between the first and second sheets in a space inside the envelope defined between the first and second sheets. The barrier member is disposed in the envelope without adhering to the first and second sheets such that the barrier member can be pulled out of the envelope through the opening. In one embodiment, the envelope is an elongate, substantially planar-shaped member having two longer peripheral edge portions and two shorter peripheral edge portions and defines only one opening at one of the shorter edge portions on the first end of the envelope. In another embodiment, the first and second sheets are connected to each other at respective peripheral portions to define the envelope and said one opening, such that a second end of the envelope which is opposite to the first end is closed, the barrier member being inserted into the envelope to span inside the envelope from the first end to the second end. In one or more preferred embodiments, the adhesion-preventing material includes chemically modified sodium hyaluronate and carboxymethylcellulose. In one or more preferred embodiments, the first sheet and second sheet of the envelope are made of cellulose or oxidized regenerated cellulose.

In accordance with another aspect of the present invention, a method of preventing adhesion of tissues following a surgical closure includes disposing a surgical device at the site of an intended surgical closure. The surgical device includes an envelope of bioabsorbable material having a first sheet connected to a second sheet and defining at least one opening between said sheets at a first end of the envelope. A layer of bioabsorbable adhesion-preventing material is disposed on the first sheet on an exterior surface of the envelope. The adhesion-preventing material is placed or disposed on tissue underlying the site of the intended closure. A rigid or semi-rigid barrier member is at least partially disposed between the first and second sheets in a space inside the envelope defined between the first and second sheets. The barrier member is disposed in the envelope without adhesion to the first and second sheets such that the barrier member can be pulled out of the envelope through the opening. In the method, after the surgical device is placed at the site of the intended surgical closure, the surgical closure is performed towards completion. Prior to completion of the surgical closure, the barrier member is pulled from the envelope out of the surgical device and away from the closure. The surgical closure is then completed leaving the envelope and adhesion-preventing material inside the closure. In one embodiment of the method, the envelope defines only one opening, and the first and second sheets are connected to each other at respective peripheral portions to define the envelope and one opening, such that a second end of the envelope which is opposite to the first end is closed, and the barrier member is inserted into the envelope to span completely across the envelope from the first end to the second end. In one or more preferred embodiments, the adhesion-preventing material includes chemically modified sodium hyaluronate and carboxymethylcellulose. In one or more preferred embodiments, the first sheet and second sheet are made of cellulose or oxidized regenerated cellulose.

In accordance with another embodiment of the present invention, a surgical device includes a rigid or semi-rigid barrier member having an elongate, substantially planar shape. A layer of bioabsorbable adhesion-preventing material is coupled to an exterior surface of the rigid or semi-rigid barrier member by a controlled adhesive member disposed between the barrier member and the adhesion-preventing material The controlled adhesive layer can be removed from the layer of adhesion-preventing material to release the barrier member from the layer of adhesion-preventing material. In a preferred embodiment, the adhesion-preventing material includes chemically modified sodium hyaluronate and carboxymethylcellulose.

In accordance with still another aspect of the present invention, a method of preventing adhesion of tissues following a surgical closure includes disposing a surgical device at the site of an intended surgical closure, which device includes a rigid or semi-rigid barrier member having an elongate, substantially planar shape. A layer of bioabsorbable adhesion-preventing material is coupled to an exterior surface of the rigid or semi-rigid barrier member by a controlled adhesive member disposed between the barrier member and the adhesion-preventing material The controlled adhesive layer can be removed from the layer of adhesion-preventing material to release the barrier member from the layer of adhesion-preventing material. In the method, the adhesion-preventing material is placed or disposed on tissue underlying the site of the intended closure. The surgical closure is then performed towards completion. Prior to completion of the surgical closure, the barrier member is separated from the layer of adhesion-preventing material by pulling the controlled adhesive member to release the barrier member from the layer of adhesion-preventing material. The surgical closure is then completed leaving the layer of adhesion-preventing material inside the closure. In one or more preferred embodiments, the adhesion-preventing material includes chemically modified sodium hyaluronate and carboxymethylcellulose.

In accordance with another embodiment of the present invention, a surgical device includes a rigid or semi-rigid barrier member made of bioabsorbable compressed cellulose, the barrier member having an elongate, substantially planar shape. A bioabsorbable adhesion-preventing material is coupled to an exterior surface of the rigid or semi-rigid barrier member. In one or more preferred embodiments, the adhesion-preventing material includes chemically modified sodium hyaluronate and carboxymethylcellulose.

In accordance with still another aspect of the present invention, a method of preventing adhesion of tissues following a surgical closure is provided. A surgical device is placed or disposed at the site of an intended surgical closure. The device includes a rigid or semi-rigid barrier member made of bioabsorbable compressed cellulose, the barrier member having an elongate, substantially planar shape. A bioabsorbable adhesion-preventing material is coupled to an exterior surface of the rigid or semi-rigid barrier member. The adhesion-preventing material is placed or disposed on tissue underlying the site of the intended closure. The closure is completed leaving the barrier member and layer of adhesion-preventing material inside the closure. In one or more preferred embodiments, the adhesion-preventing material includes chemically modified sodium hyaluronate and carboxymethylcellulose.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 1 illustrates a surgical device in accordance with an embodiment of the invention;

FIG. 2 illustrates a side view of the device as shown in FIG. 1 in accordance with an embodiment of the invention;

DETAILED DESCRIPTION

Figure 3:
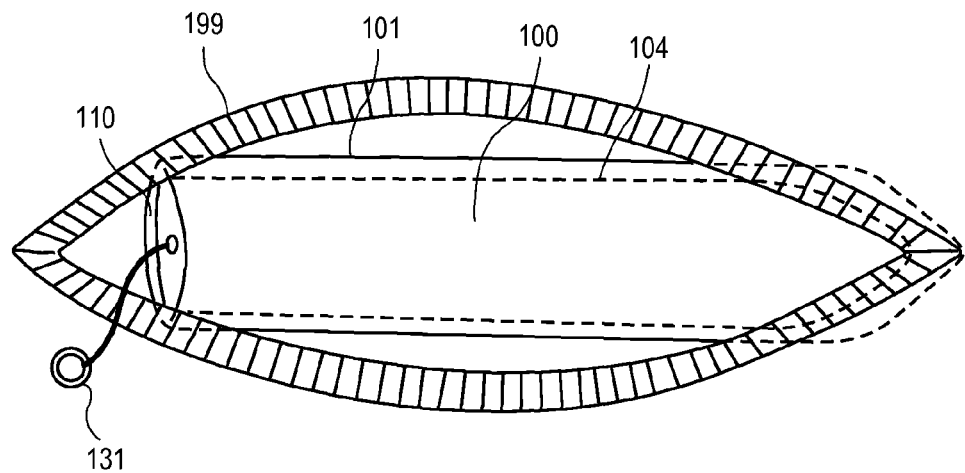
FIG. 3 illustrates a device in accordance with an embodiment of the invention inserted into a surgical incision, prior to closure of said incision.

The present invention provides, in some embodiments, a surgical medical device and method that facilitates the safe closure of surgical incisions over inner body tissue viscera, while helping to prevent the formation of postoperative adhesions. The present invention serves as a barrier to protect the underlying or viscera from injury during surgical closure of the incision, while also providing a physical layer which prevents formation of adhesions postoperatively. In an exemplary embodiment, the device of the present invention combines a rigid or semi-rigid flat barrier with a layer or sheath of product which prevents the formation of postoperative adhesions. In a method in accordance with an embodiment of the invention, the device is placed into the abdominal cavity by the surgeon prior to closure of the abdominal surgical wound over the abdominal viscera. The surgeon proceeds to close the abdominal layers in the standard fashion. Prior to completion of the surgical closure, the rigid or semi-rigid portion of the device is removed, leaving within the abdominal cavity the product which prevents adhesion formation to the abdominal wall. The device can be sterile. The device can be designed for single use.

The invention will now be described with reference to the drawing figures, in which like reference numerals refer to like parts throughout.

FIG. 1 illustrates aspects of a surgical device 100 in accordance with a first embodiment of the invention. The device 100 includes an envelope 101 made of two overlying flat layers or sheets defining at least one opening 110 on one side of the envelope 101. The envelope 101 may therefore include a first sheet 102 which is connected to a second sheet 103. The sheets may be connected to each other in any fashion, such as by stitching, adhesive, bonding, or molding. The sheets may also be directly produced or manufactured to form the envelope 101 having the at least one opening 110. In the embodiment shown in FIG. 1, the sheet 102 is connected or bonded to sheet 103 at their respective perimeters or peripheral portions, save for the edges which define opening 110. In one embodiment, an end 120 of envelope 101 is closed, which end 120 is opposite to an end defining opening 110.

The device 100 further includes a rigid or semi-rigid barrier device or member 104 which is inserted or at least partially disposed in the envelope 101. As used herein, a "barrier member" is any body which presents a generally impenetrable outer surface and/or which readily prevents the puncture or passage of another body, such as a needle, through said barrier member body, at least without the application of a substantial amount of force. As used herein, a "semi-rigid" member is any body which may readily bend or flex but which does not compress or shear like a fluid or gel. An example of a rigid device which may be utilized for barrier member 104 is a standard steel malleable retractor commonly available as a surgical instrument. An example of a semi-rigid device is a disposable plastic or rubber visceral refractor also commonly available as a surgical instrument. The barrier member 104 may be completely enclosed inside an interior space within the envelope 101 such as shown in FIG. 1, or may be partially disposed inside said interior space. The barrier member 104 may completely fill the interior space, and may extend along the entire length of the envelope from a first end 111 to a second end 112, or may be sized to define or leave some spacing between the barrier member 104 and the boundaries of the interior space defined by envelope 101.

The envelope 101 made of sheets or layers 102, 103 may be made of a material which prevents the formation of postoperative adhesions. Alternatively, in an exemplary embodiment, an additional layer 105 of adhesion-preventing material may be applied to one or both of sheets 102, 103, as illustrated in FIG. 2. All components of the device 100 may be sterile. The envelope 101, including each of sheets 102 and 103, and any additional layer such as layer 105, is preferably biocompatible and bioabsorbable. In a preferred embodiment of the invention, sheets 102, 103 are made of a material which will not adhere to the inner barrier member 104, in order to facilitate withdrawal of the rigid or semi-rigid barrier member 104 out of the envelope 101 of the device 100 prior to completion of the surgical closure. In this regard, the inner barrier member 104 is not attached to sheets 102, 103, or envelope 101 in general, except for a minimal friction fit which holds the parts of assembly 100 together prior to application into a surgical incision. In an embodiment, the sheets 102, 103 may be made of cellulose or oxidized regenerated cellulose. In an embodiment, the adhesion-preventing material formed in sheets 102 or 103, or within layer 105, may include chemically modified sodium hyaluronate and carboxymethylcellulose, or another suitable adhesion preventing material which is also bioabsorbable and biocompatible. In alternative embodiments, the adhesion preventing material, such as used in layer 105, may include other compounds or materials used in conjunction with either sodium hyaluronate or carboxymethylcellulose, separately or in combination. In an exemplary embodiment, the chemically modified sodium hyaluronate and carboxymethylcellulose material may be a bioresorbable, translucent adhesion barrier composed of two anionic polysaccharides, sodium hyaluronate (HA) and carboxymethylcellulose (CMC), each of which has been chemically modified with the activating agent 1-(3-dimethylaminopropyl)-3-ethylcarbodiimide hydrochloride (EDC), such as provided in SEPRAFILM® brand adhesion barrier material manufactured by Genzyme Corporation, Cambridge, Mass. Possible other materials which may be considered adhesion-preventing for use in the present invention include omega-3 fatty acid impregnated or coated materials. Layer 105 may be stitched, bonded, or otherwise connected or adhered to at least sheet 103. Another layer of adhesion-preventing material (not shown) may also be applied or disposed over sheet 102.

In the embodiment illustrated in FIG. 1, the envelope 101 may preferably be an elongate, substantially planar-shaped member having two longer peripheral edge portions 121, 122 and two shorter peripheral edge portions 123, 124 and which defines only one opening 110 at short edge portion 123 on first end 111 of the envelope 101. In this regard, the envelope may be substantially rectangular shaped, although any planar shape may be embodied in the invention.

In using the invention during closure of a surgical incision, it is important that the planar area spanned by the invention adequately cover the span or area of tissue underlying and around the incision where post-operative adhesions may occur. As such the device 100 must be sufficiently long to span at least as long as any desired incision, but must also be wide enough to cover both the areas into which surgical tools or instruments (such as suture needles) may be used to effect closure of the incision, so that the device 100 adequately protects the underlying tissue via the barrier member 104. The width of the device must also be sufficient to provide the intended protection against post-operative tissue adhesions. Accordingly, a preferred aspect ratio (defined herein as length over width) of the planar assembly of the invention 100 and/or envelope 101 may range from 2 to 10, while a more preferred aspect ratio may range from 3 to 5.

In an embodiment, the first and second sheets 102, 103 of envelope 101 are connected to each other at respective peripheral portions, demarcated at least by longer edge portions 121 and 122, to define the envelope 101 and said opening 110, as well as the space inside the envelope 101 into which the barrier member 104 is disposed. In the embodiment shown in FIG. 1, a second end 112 of the envelope 101 which is opposite to the first end 111 is closed. In an embodiment, the barrier member 104 can be disposed in the envelope 101 to extend from the first end to the second end of said envelope, to span substantially the entire length of the envelope. In other embodiments, each of first sheet 102 and/or second sheet 103 may extend past any point of connection between said sheets, such that the envelope 101 defines at least an inner space or pocket for receiving the inner barrier member 104, but one or more portions of the sheets of bioabsorbable material and any layer of bioabsorbable adhesion-preventing material disposed thereon extend outwards, similar to a planar peripheral skirt around envelope 101, to provide a larger area to be covered by device 100, thereby enabling the device 100 to help prevent post-operative adhesions over a wider area of tissue.

The device 100 may further include a means for retracting or pulling the inner barrier member 104 out of the envelope 101. In one embodiment a string or cord 130 may be attached to one end of the barrier member 104 which can be pulled by a ring or other grip member 131 at an end of cord 130 which is disposed outside any incision in which the device 100 is placed. Other suitable means for retracting may also be used, such as, by example, an elongated handle, ribbon, or chain.

Figure 4:
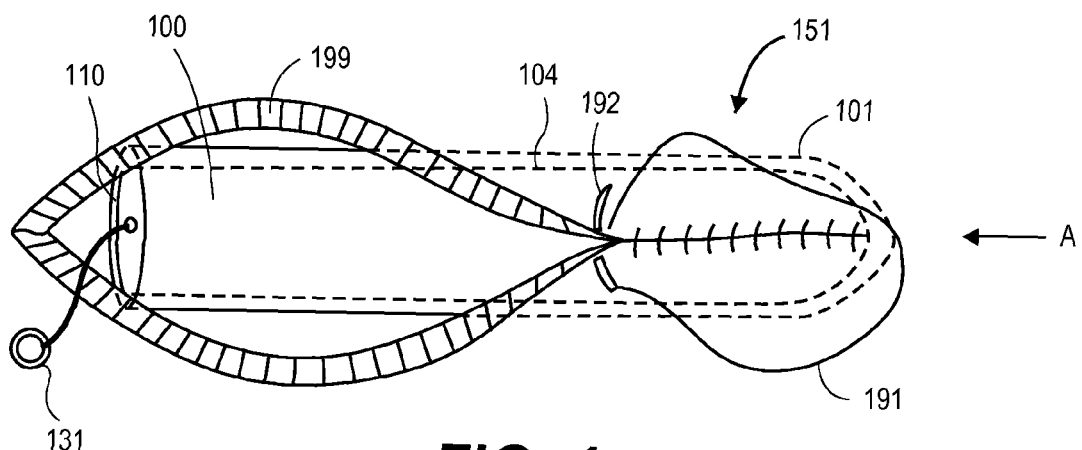
FIG. 4 illustrates a device in accordance with an embodiment of the invention inserted into a surgical incision, during closure of said incision.
Figure 5:
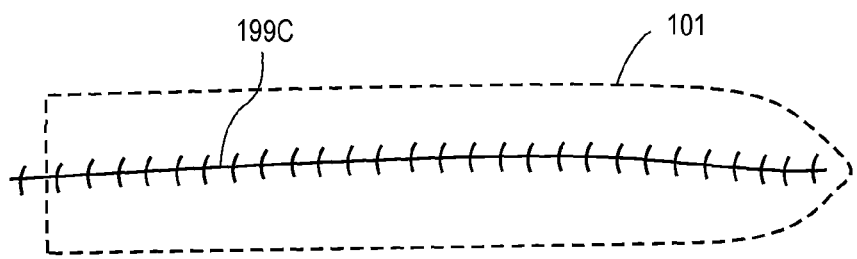
FIG. 5 illustrates a device in accordance with an embodiment of the invention inserted into a surgical incision, after closure of said incision, and after the inner barrier element has been withdrawn from the device.

The present invention also provides a method of preventing adhesion of tissues following a surgical closure. As used herein, a "surgical closure" shall mean any closure of an opening or incision during a surgical or medical procedure on any human or mammalian body. In a preferred embodiment, the method of the invention includes the initial step of disposing a surgical device at the site of an intended surgical closure, such as shown in FIG. 3. In FIG. 3, the device 100 is inserted over the viscera inside an open incision 199. Layer 105, made of adhesion-preventing material as discussed herein, is disposed on top of exposed visceral organs or tissue underlying the site of the intended closure. The surgical closure is then performed towards completion, as shown in FIG. 4, such as by suturing the incision closed under standard surgical practice with a suture 191 and suture needle 192. As can be seen in FIG. 4, while the incision 199 is being closed, distal portions 151 of the device 100 opposite to opening 110, including portions of envelope 101 and inner barrier member 104, may remain inside the closure within the body. While the surgical closure is performed, the barrier member 104 acts as a shield to the tissue underlying the device 100, to help prevent accidental injury to such tissue by surgical instruments, such as suture needle 192. Prior to completion of the surgical closure, the barrier member 104 is pulled using means 131 out from the envelope 101, generally in the direction "A" shown in FIG. 4, away from site of the surgical closure. The completed closure 199c eventually has the envelope 101 and adhesion-preventing material 105 attached to said envelope 101 left inside the closure within the body. The envelope 101 and adhesion-preventing material 105 are bioabsorbable and eventually dissolve and are absorbed by the body. The adhesion-preventing material 105 helps to prevent formations of adhesions between the underlying viscera and any overlying tissue which has been closed or sutured together, such as the abdominal wall.

Figure 6:
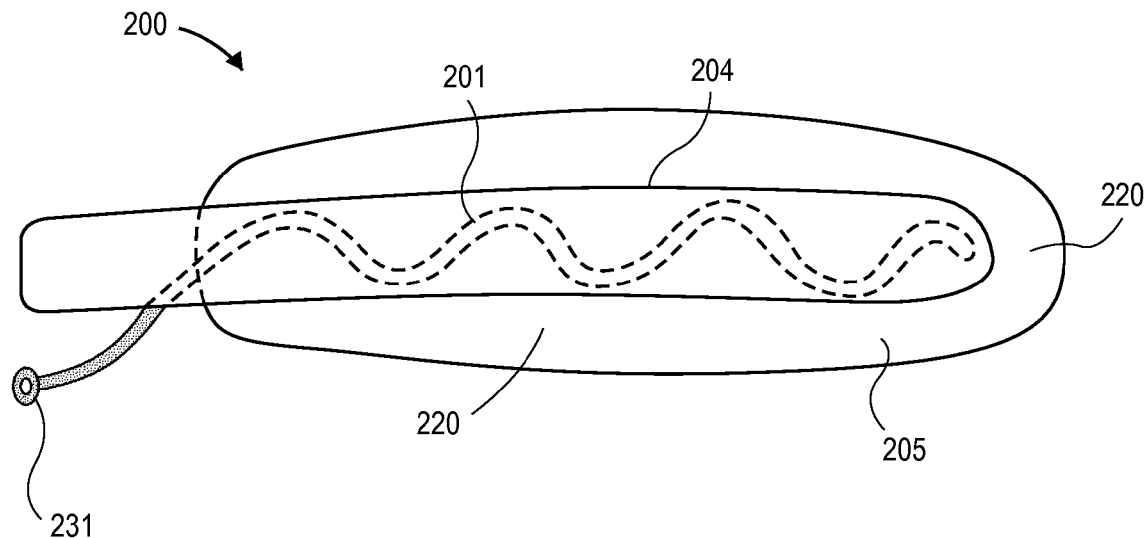
FIG. 6 illustrates a surgical device in accordance with another embodiment of the invention.

FIG. 6 illustrates a surgical device in accordance with another embodiment of the invention. Device 200 includes a rigid or semi-rigid barrier member 204 having an elongate, substantially planar shape. A layer of bioabsorbable adhesion-preventing material 205 is coupled to an exterior surface of the rigid or semi-rigid barrier member 204 by a controlled adhesive member 201 disposed between the barrier member 204 and the adhesion-preventing material 205. The controlled adhesive layer 201 can be pulled out from between the barrier member 204 and the layer of adhesion-preventing material 205 to release the barrier member 204 from the layer of adhesion-preventing material 205. In one embodiment, the barrier member 204 can be a rigid, flat device, and the adhesion-preventing material 205 can be bonded to one side of the rigid or semi-rigid flat device. In one embodiment, the adhesion-preventing material 205 can include chemically modified sodium hyaluronate and carboxymethylcellulose. The barrier member 204 can be a rigid or malleable steel refractor. In one embodiment, the adhesion-preventing material 205 may only be disposed to cover one exterior side of the barrier member 204. In an embodiment as shown in FIG. 6, the layer of adhesion-preventing material 205 may extend in area beyond the perimeter of the barrier member 204, to form a peripheral skirt 220 about the barrier member 204, which peripheral extension or skirt may form any suitable shape for use in closure of a surgical incision, in order to help prevent the formation of post-operative incisions. The controlled adhesive 201 may be any suitable adhesive material which provides enough adhesion between member 204 and layer 205 to enable the device 200 to be handled for proper insertion and positioning inside the site of an intended surgical closure, while being capable of being removed from layer 205, without significantly affecting the integrity of layer 205, to enable the barrier member 204 to be readily separated or released from the layer 205. The controlled adhesive may be incorporated into an element, such as an adhesive impregnated or coated yarn or thread. In one embodiment, as is shown in FIG. 6, the controlled adhesive layer 201 may be shaped as an elongate, thin, string-like formation, which can be pulled by a gripping means 231.

In an embodiment of the invention, a method of preventing adhesion of tissues following a surgical closure includes disposing surgical device 200 at the site of an intended surgical closure, such as in, for example, the abdomen, the adhesion-preventing material 205 being disposed on viscera or tissue underlying the site of the intended closure. The surgical closure is performed towards completion, but prior to completion of the surgical closure, the barrier member 204 is separated from the layer of adhesion-preventing material 205 by removing the controlled adhesive member 201 from the layer of adhesion-preventing material 205 to release the barrier member 204 from the layer of adhesion-preventing material 205. The surgical closure is then completed and leaving the layer of adhesion-preventing material 205 inside the closure, which is eventually dissolved. In order to be most useful during a surgical closure, the aspect ratio of the device 200 and/or layer 205 including skirt 220 may range from 2 to 10, while a more preferred aspect ratio may range from 3 to 5.

Figure 7:
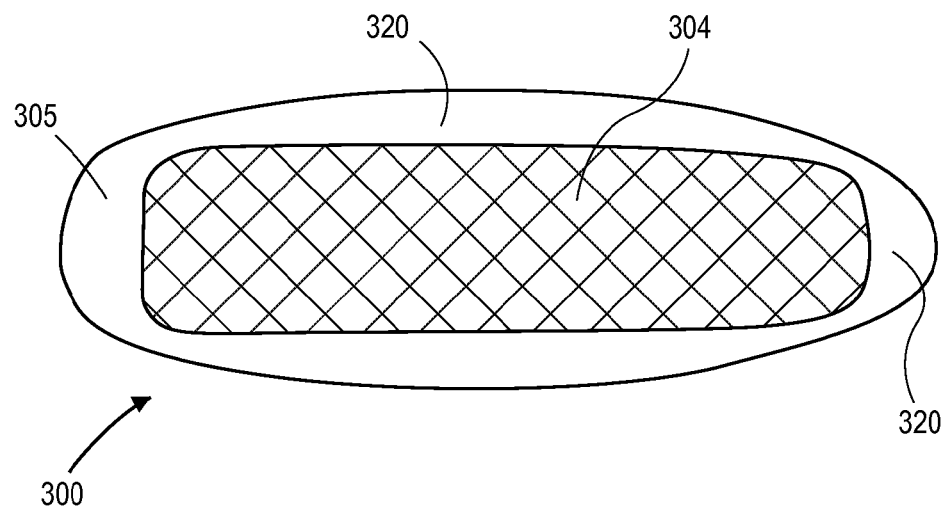
FIG. 7 illustrates a surgical device in accordance with another embodiment of the invention.

FIG. 7 illustrates a surgical device in accordance with another embodiment of the invention. The device 300 includes a rigid or semi-rigid barrier member 304 made of bioabsorbable compressed cellulose, or similar bioabsorbable, biocompatible substance. In an embodiment, the barrier member 304 may have an elongate, substantially planar shape. A bioabsorbable adhesion-preventing material 305 is bonded or coupled to at least one side or an exterior surface of the barrier member 304. In one embodiment, the adhesion-preventing material 305 may only be disposed to cover one exterior side of the barrier member 304. In an embodiment as shown in FIG. 7, the layer of adhesion-preventing preventing material 305 may extend in area beyond the perimeter of the barrier member 304, to form a peripheral skirt 320 about the barrier member 304, which peripheral extension or skirt may form any suitable shape for use in closure of a surgical incision, in order to help prevent the formation of post-operative incisions. In an embodiment, the adhesion-preventing material 305 can include chemically modified sodium hyaluronate and carboxymethylcellulose.

In an embodiment of the invention, a method of preventing adhesion of tissues following a surgical closure includes disposing device 300 at the site of an intended surgical closure, the adhesion-preventing material 305 being disposed on tissue underlying the site of the intended closure. The surgical closure may then be completed leaving the entire device 300, including barrier member 304 and the layer of adhesion-preventing material 305 inside the closure, both of which are bioabsorbable and may eventually dissolve harmlessly in the body. In order to be most useful during a surgical closure, the aspect ratio of the device 300 and/or layer 305 including skirt 320 may range from 2 to 10, while a more preferred aspect ratio may range from 3 to 5.

The many features and advantages of the invention are apparent from the detailed specification, and thus, it is intended by the appended claims to cover all such features and advantages of the invention which fall within the true spirit and scope of the invention. Further, because numerous modifications and variations will readily occur to those skilled in the art, it is not desired to limit the invention to the exact construction and operation illustrated and described, and accordingly, all suitable modifications and equivalents may be resorted to falling within the scope of the invention.

The invention claimed is:

1. A method of preventing adhesion of tissues following a surgical closure, comprising:

disposing a surgical device at the site of an intended surgical closure on a visceral side underlying the closure, the surgical device having an envelope comprising a first layer of bioabsorbable material having a first sheet connected to a second sheet and defining at least one opening between said sheets at a first end of the envelope, wherein the bioabsorbable material of the first layer includes cellulose or oxidized regenerated cellulose;

the envelope further comprising a second, additional layer, made of bioabsorbable adhesion-preventing material, disposed on the first sheet or second sheet of the first layer on an exterior surface of the envelope, the adhesion-preventing material being disposed on tissue on the visceral side underlying the site of the intended closure, wherein the bioabsorbable adhesion-preventing material of the second, additional layer comprises chemically modified sodium hyaluronate and carboxymethylcellulose, or omega-3 fatty acid impregnated material, or omega-3 fatty acid coated material, or a combination thereof;

a rigid or semi-rigid planar barrier member which does not compress like a fluid, and which prevents puncture or passage of a needle through said member during said surgical closure, at least partially disposed between the first and second sheets in a space inside the envelope defined between the first and second sheets, the barrier member being disposed in the envelope without adhering to the first and second sheets formed by the first layer of the envelope, such that the barrier member can be pulled out of the envelope through the opening without adhering to the envelope; and wherein the second, additional layer of adhesion-preventing material is prevented from sticking to, or being displaced by, the barrier member, due to the first or second sheet of the first layer of the envelope being disposed between the barrier member and the second, additional layer of adhesion-preventing material;

performing the surgical closure towards completion along an incision over a span directly overlying the planar barrier member while said barrier member is disposed over tissue underlying the site of the intended closure;

prior to completion of the surgical closure, pulling the barrier member from the envelope out of the surgical device and away from the closure; and completing the surgical closure and leaving the envelope and adhesion-preventing material inside the closure.

2. The method of claim 1, wherein the envelope defines only one opening, and the first and second sheets are connected to each other at respective peripheral portions to define the envelope and one opening, such that a second end of the envelope which is opposite to the first end is closed, and wherein the barrier member is inserted into the envelope to span completely across the envelope from the first end to the second end.

* * * * *